(12) United States Patent
Bakris

(10) Patent No.: US 9,517,050 B2
(45) Date of Patent: Dec. 13, 2016

(54) APPARATUS FOR DISPENSING GEL FOR USE WITH A MEDICAL DEVICE

(71) Applicant: Nicholas C. Bakris, Kileen, TX (US)

(72) Inventor: Nicholas C. Bakris, Kileen, TX (US)

( * ) Notice: Subject to any disclaimer, the term of this patent is extended or adjusted under 35 U.S.C. 154(b) by 0 days.

(21) Appl. No.: 14/618,507

(22) Filed: Feb. 10, 2015

(65) Prior Publication Data

US 2015/0150532 A1   Jun. 4, 2015

Related U.S. Application Data

(63) Continuation-in-part of application No. 13/329,783, filed on Dec. 19, 2011, now abandoned.

(51) Int. Cl.
*A61B 8/14* (2006.01)
*A61B 8/00* (2006.01)
*A61M 35/00* (2006.01)

(52) U.S. Cl.
CPC ............ *A61B 8/4281* (2013.01); *A61B 8/4405* (2013.01); *A61M 35/00* (2013.01)

(58) Field of Classification Search
CPC .. A61M 35/003; A61B 5/0402; A61B 8/4281; G01K 11/03
USPC ..................... 222/95, 146.2–146.5
See application file for complete search history.

(56) References Cited

U.S. PATENT DOCUMENTS

| | | | | |
|---|---|---|---|---|
| 4,699,296 A | * | 10/1987 | Schrock, Jr. ........ | A61M 5/1417 222/155 |
| 4,844,080 A | * | 7/1989 | Frass ...................... | G01N 29/28 600/437 |
| 5,568,810 A | * | 10/1996 | Hamers ................. | A61B 8/4281 128/898 |
| 6,561,389 B1 | * | 5/2003 | Earle .................... | B65D 83/0005 222/146.5 |
| 7,975,879 B2 | * | 7/2011 | Groesbeck ........... | B65D 5/4204 220/4.01 |
| 8,752,734 B2 | * | 6/2014 | Smith .................. | B67D 3/0054 222/105 |
| 2005/0077318 A1 | * | 4/2005 | Macler ...................... | B67B 7/28 222/81 |
| 2007/0062932 A1 | * | 3/2007 | Saha ....................... | A45D 34/04 219/521 |
| 2011/0190635 A1 | * | 8/2011 | Bosler .................. | A61B 8/4281 600/458 |

FOREIGN PATENT DOCUMENTS

JP          2006320497 A   * 11/2006

* cited by examiner

*Primary Examiner* — Patrick M Buechner
(74) *Attorney, Agent, or Firm* — The Weintraub Group, P.L.C.

(57) ABSTRACT

An apparatus for dispensing gel for use with a medical device comprising a storage container for storing a quantity of gel of at least one gallon, a pump for delivering gel to a user, a first delivery conduit connected to the outlet of the storage container and the inlet of the pump, and a second delivery conduit connected to the outlet of the pump on one end and having a second end terminating at a location near the patient. The apparatus includes a heat source positioned proximal to the storage container for warming the gel so that is at a comfortable temperature when it is applied to a patient.

8 Claims, 3 Drawing Sheets

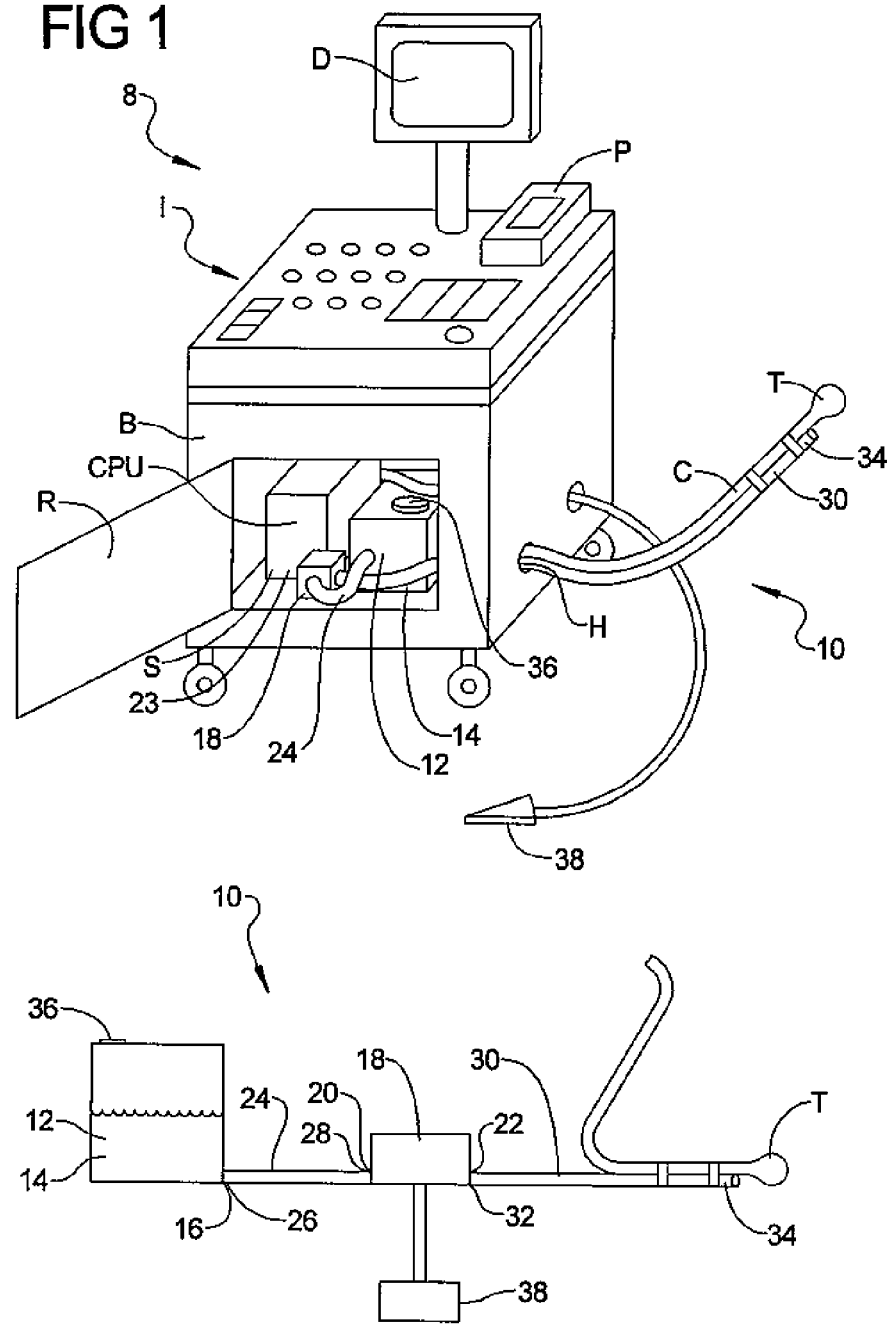

FIG 3
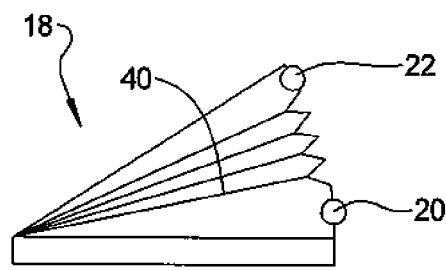
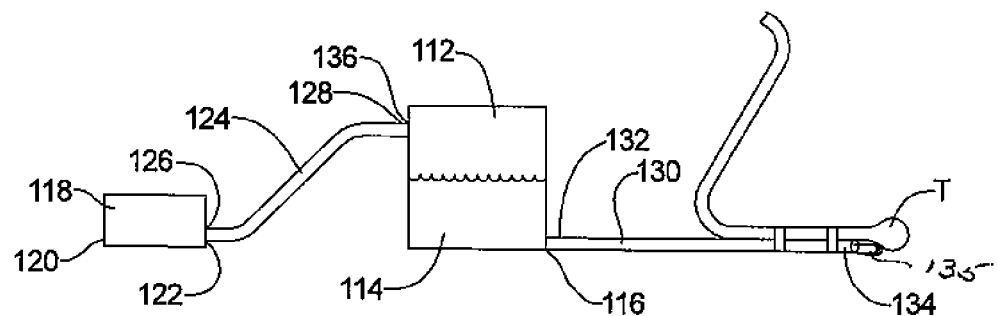
FIG 4

APPARATUS FOR DISPENSING GEL FOR USE WITH A MEDICAL DEVICE

CROSS-REFERENCE TO RELATED APPLICATION

This application is related to the subject matter of co-pending U.S. application Ser. No. 13/329,783, which was filed on Dec. 19, 2011, which claims the benefit of International Application No. PCT/US2010/039317, filed Jun. 21, 2010, the entire disclosures of which are hereby incorporated by reference.

BACKGROUND OF THE INVENTION

1. Field of the Invention

The present invention pertains to an apparatus for dispensing gel. More particularly, the present invention pertains to an apparatus for dispensing gel for use with an ultrasound device. Even more particularly, the present invention pertains to an apparatus for dispensing warmed gel for use with an ultrasound device.

2. Description of the Prior Art

It is routine to perform medical diagnostic or therapeutic procedures which require the application of a gel onto the patient's skin. In order to perform these procedures, an ultrasound machine often requires that the patient have a layer of gel first applied to their skin around the area of examination. The gel is typically contained within a plastic squeeze bottle, or tube, which the ultrasound technician uses to apply the gel onto the patient. The gel is relatively cool to the touch, and therefore, rather uncomfortable for the patient. In addition, using a squeeze bottle can be awkward for the technician because the bottle may require two hands to squeeze and may therefore be cumbersome and difficult to use.

Often the health care provider needs to apply additional gel during the procedure. This requires the technician to stop the procedure, apply the additional gel, and then relocate the ultrasound image. But actually locating the proper image is time consuming and often the most difficult part of the procedure, and therefore it can be very inefficient and inconvenient to stop and re-apply additional gel.

Efforts have previously been made to solve some of these problems. For instance, ultrasound devices have been devised in which the ultrasound transducer dispenses gel, such as found in U.S. Patent Publication No. 2008/0281206 to Bartlett et al. The transducer disclosed by Bartlett includes a small portable pocket which contains the gel. The user squeezes the gel out of the pocket through a nozzle by pressing on the pocket. Although gel is delivered to the patient from the transducer, the pocket can only store a very small volume of gel, and it is not warmed.

In addition, another ultrasound device which dispenses gel is disclosed in U.S. Patent Publication No. 2009/0048514 to Azhari et al. In Azhari, there is an electromechanical box located near the computer of the ultrasound which dispenses the gel to the transducer. However, the device disclosed by Azhari does not allow the technician to dispense the gel while positioned away from the device, nor does it dispense gel which has been warmed.

Thus, there remains a need for an ultrasound device which is capable of dispensing warmed gel to the patient, and which enables the technician to dispense the gel from a location close to the patient.

The present invention, as is detailed hereinbelow, seeks to resolve these issues by providing an apparatus for dispensing gel for use with an ultrasound device.

SUMMARY OF THE INVENTION

A first embodiment of the present invention provides an apparatus for dispensing gel for use with an ultrasound device comprising:

(a) a storage container for storing a quantity of gel of at least one gallon, the storage container having an outlet for exiting the gel from the storage container;

(b) a pump for delivering gel to a user, the pump having an inlet and an outlet;

(c) a first delivery conduit having a first end and a second end, the first end being connected to the outlet of the storage container and the second end being connected to the inlet of the pump;

(d) a second delivery conduit having a first end and a second end, the first end being connected to the outlet of the pump and the second end terminating at a location near the patient;

(e) a heat source positioned proximal to the storage container for heating the gel to a temperature of about 80° F.-100° F.; and wherein activating the pump delivers warmed gel to the second end of the second delivery conduit.

In a second embodiment of the present invention, an apparatus is provided for dispensing gel for use with an ultrasound device comprising:

(a) a storage container for storing a quantity of gel of at least one gallon, the storage container having an inlet and an outlet;

(b) a pump for delivering a gaseous fluid to the storage container, the pump having an inlet and an outlet;

(c) a first delivery conduit having a first end and a second end, the first end being connected to the outlet of the pump and the second end being connected to the inlet of the storage container;

(d) a second delivery conduit having a first end and a second end, the first end being connected to the outlet of the storage container and the second end terminating at a location near the patient;

(e) a heat source positioned proximal to the storage container for heating the gel to a temperature of about 80° F.-100° F.; and wherein activating the pump delivers warmed gel to flow out of the second end of the second delivery conduit.

In a third embodiment of the present invention, an apparatus is provided for dispensing gel for use with a medical device comprising:

(a) a collapsible storage container for storing a quantity of gel of at least one gallon, the storage container having an outlet;

(b) a housing having an interior chamber for housing the storage container;

(c) a pump for pressurizing the interior chamber with a gaseous fluid to the storage container, the pump having an inlet and an outlet, and the pump outlet being in fluid communication with the interior chamber;

(d) a delivery conduit having a first end and a second end, the first end being connected to the outlet of the storage container and the second end extending outwardly of the housing to a distal location; and (e) a heat source for heating the gel to a temperature of about 80° F.-100° F.

The medical device is preferably an ultrasound machine which includes a transducer for transmitting and receiving sound waves, a computer, and a cord for transmitting data between the transducer and the computer. The ultrasound machine may also include: (a) a portable wheeled cabinet; (2) a visual display for displaying output data such as images; (3) an input device such as a keyboard or a mouse which allows the technician to operate the ultrasound machine and input data thereto; (4) a disk storage device for storing data; (5) and a printer for creating a hard print copy of the output data.

Preferably, the heat source for warming the gel is the computer. However, the heat source may include a separate heating element. The storage container housing the gel is located close to the computer so that heat generated by the computer transfers to the gel. As such, the storage container has thin walls and/or is made from a material which conducts heat well, and/or is vented to facilitate the heat transfer.

The pump used herein may be either manually-operated or driven by a power source. When a manually-operated pump is provided, the pump can comprise the type having an internal compartment which has an expandable/compressible volume (e.g. similar to that of an accordion or bellows), and the inlet and outlet can each comprise a check for directing flow through the pump in one direction. The inlet check valve allows a fluid (either gaseous fluid or gel depending upon the embodiment) to flow only into the compartment, and the outlet check valve allows the fluid to flow only out of the compartment.

When manually operated, the technician successively expands and contracts the internal compartment which draws fluid in through the inlet check valve and forces fluid out through the outlet check valve, which delivers the warmed gel to the second end of the second conduit.

When the pump is driven by a power source it can include a switch (or any other suitable means) for activating the pump. The pump may be of any type which is well-known in the art and suitable for use herewith, such as a positive displacement or dynamic pump. The switch may be located remotely from the pump, such as on the floor (e.g., as a foot-activated switch), or located on, or near to, the transducer and being operable by hand.

For a more complete understanding of the present invention, reference is made to the following detailed description and accompanying drawing. In the drawing, like reference characters refer to like parts throughout the views in which:

BRIEF DESCRIPTION OF THE DRAWINGS

FIG. 1 is a perspective view of a first embodiment of the present invention hereof;

FIG. 2 is a schematic drawing of the first embodiment hereof;

FIG. 3 is an enlarged view showing an example of a manually-operated pump for use herewith;

FIG. 4 is a schematic drawing of the second embodiment; and

DETAILED DESCRIPTION OF THE PREFERRED EMBODIMENT

Figure 5:
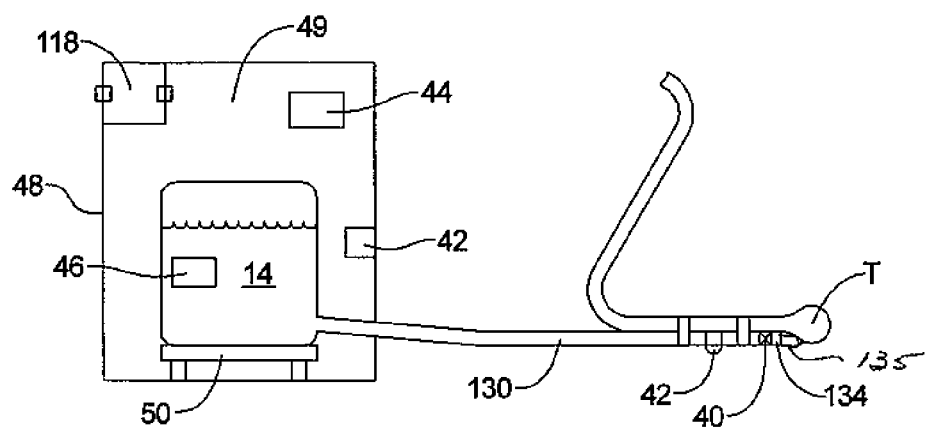
FIG. 5 is a schematic drawing of the third embodiment.

At the outset it is to be noted that although the ensuing disclosure is made with reference to ultrasound devices for use in the medical field, the present invention is not so limited. The apparatus may also be used with any other medical equipment for various other procedures in which a fluid, such as a gel, is applied to a patient. For example, the apparatus can be used with procedures in which a probe or a sensor is secured to a patient's skin, such as with an electrocardiogram (EKG) or for electrotherapy. Furthermore, the present invention can be used in any suitable application not related to the medical field in which a warmed fluid is desired to be delivered to a location which is remote from the fluid's storage container.

Referring to FIG. 1, a typical ultrasound machine contemplated for use herein is of the type which is well-known in the art, and which is used for providing a variety of medical services and procedures, such as in the fields of cardiology, endocrinology, gastroenterology, obstetrics, ophthalmology, etc. Generally, the ultrasound machine 8 comprises a transducer T for transmitting and receiving sound waves, a computer CPU, and a cord C for transmitting data between the transducer T and the computer CPU. The ultrasound machine 8 may also comprise a visual display D for displaying output data such as images, an input device I such as a keyboard, a mouse, a rollerball, etc. which allows the user to operate the ultrasound machine 8 and to input data therein, a disk storage device S for storing data, a cabinet B for housing at least some of the ultrasound machine 8 components such as the computer, and a printer P for creating a hard print copy of the output data.

When a cabinet B is provided, it may include at least one door R for accessing and enclosing the interior of the cabinet B, a plurality of wheels for moving the cabinet B, and at least one hole H, or opening, to provide access for wiring, tubing, or the like.

In accordance with a first embodiment of the present invention, and as shown generally in FIG. 1 and schematically in FIG. 2, there is provided an apparatus 10 for delivering warmed gel to the transducer T of an ultrasound machine 8. The apparatus 10 comprises: (a) a storage container 12 for storing a quantity of gel 14 of at least one gallon, the storage container 12 having an outlet 16 for exiting the gel 14 from the storage container 12; (b) a pump 18 for pumping the gel 14 to a location near the transducer T, the pump 18 having an inlet 20 and an outlet 22; (c) a disposable first conduit 24 having a first end 26 and a second end 28, the first end 26 punctured into the outlet 16 of the storage container 12 and the second end 28 connected to the inlet 20 of the pump 18; (d) a disposable second conduit 30 having a first end 32 connected to the pump 18 and a second end 34 secured to the transducer T; and (e) a heat source 23 positioned proximal to the storage container 12 for heating the gel 14, wherein activating the pump 18 causes gel 14 to flow out of the storage container 12, through the first conduit 24, through the pump 18, through the second conduit 30, and to the patient.

The gel further flows through a disposable straw attached to the second end of the disposable second conduit. By dispersing the gel through a disposable straw, it allows for a new straw to be used for each patient. This ensures that the device maintains cleanliness between use and will also help the device be in compliance with Joint Commission standards.

The storage container 12 for housing the gel 14 is of any suitable shape for storing a fluid, such as a rectangular closed box, a cylindrical container, or a container having a slanted or conical bottom in which the fluid is funneled to a particular area as the level of fluid gets low. The storage container 12 is formed from materials which are generally impervious to fluids and non-reactive with the gel 14. Preferably, the storage container 12 is formed from a polymer such as polycarbonate, HDPE, LDPE, ABS, nylon, PETE, or the like. The storage container 12 can be collapsible under its own weight, such that it collapses as gel 14 is removed from its contents. As understood by one having ordinary skill in the art, gel is commonly supplied by gel manufacturers in such a container. The storage container 12 can also be of a rigid construction such that it retains its shape as gel 14 exits the storage container 12. Furthermore, since heat is transferred from the heat source 23 to the gel 14 stored in the storage container 12 (as discussed in further detail below), the storage container 12 preferably has a thin-wall construction or is ventilated to facilitate the transfer of heat, and/or it is formed from a material which has superior heat conductivity characteristics.

As shown in greater detail in FIG. 2, the storage container 12 has an outlet 16 which is connected to the first end 26 of the first conduit 24. The gel 14 is drawn through the outlet 16 and into the first conduit 24 by the pump 18, as discussed further below. The storage container 12 can also have an inlet 36. The inlet 36 can comprise a vent which allows air to enter the storage container 12 as gel 14 exits the container 12. The inlet 36 may also comprise a sealed door or lid, which may be opened to refill the storage container 12 with gel 14 when the level is low. Alternatively, the storage container 12 can be refilled with gel 14 through the outlet 16 by first disconnecting the first conduit 24 therefrom, or the storage container 12 can be disposable and replaced by a full replacement storage container 12 as well.

The gel 14 can be any suitable type of gel which is well known and commonly used in conjunction with the medical procedures and equipment described herein, for example, the ultrasound transmission gel sold under the trademark AQUASONIC 100®. It is known that suitable gels will be aqueous, non-scented, hypoallergenic, bacteriostatic, non-sensitizing, and non-irritating.

A heat source 23 is provided to warm the gel 14 housed in the storage container 12. The storage container 12 should be located in close proximity to the heat source 23 to effectuate heat transfer from the heat source 23 to the gel 14. The heat source 23 can comprise any suitable type of heat source which is well-known to one having ordinary skill in the art, including a heater, a heating blanket, a warming plate, and so forth. Preferably the heat source 23 is the computer. Preferably the heat source 23 warms the gel to a temperature of about 80° F.-100° F., which is typically a gradient temperature increase of about 8° F.-32° F. over the ambient temperature in a room.

The elongated first conduit 24 has a first end 26 and a second end 28. The first end 26 is secured to the outlet 16 of the storage container 12. The second end 28 of the first conduit 24 is connected to the pump 18. The conduit 24 is connected to both the storage container 12 and the pump 18 by any suitable means which are well-known in the art, such as by compression fittings, threaded bulkhead fittings, or the like.

The pump 18 is provided for pumping warmed gel 14 from the storage container 12 to the transducer T via the first and second conduits, 24 and 30, respectively. The pump 18 has an inlet 20 and an outlet 22, the inlet 20 being connected to the first conduit 24, and the outlet 22 being connected to the second conduit 30. The outlet 22 and the second conduit 30 are secured together in the same manner as described above regarding the first conduit 24 and the pump 18. As discussed further below, the pump 18 may be any suitable type of pump which is well-known in the art, and may be either manually-operated or powered electrically, pneumatically, hydraulically, or by any other suitable means.

The second conduit 30 is provided to transport the gel 14 from the pump 18 to the patient. As discussed above, the first end 32 of the conduit 30 is secured to the outlet 22 of the pump 18. The second end 34 of the second conduit 30 is secured to the transducer T to deliver the gel 14 to the patient. The second end 34 of the second conduit 30 is secured to the transducer T by any suitable means, such as by C-clamps, plastic cable ties (or zip ties), elastomeric bands, hook-and-loop connectors such as the type sold under the trademark Velcro®, or any other suitable means which are known in the art. Alternatively, the second conduit 30 can be formed integrally with the transducer T.

The first conduit 24 and second conduit 30 are formed from a polymer which is generally impervious to liquids and nonreactive with the gel 14, and are preferably formed from a flexible polymer, such as vinyl.

According to this embodiment, when a powered pump is provided, the pump 18 receives gel 14 from the storage container 12 via the first conduit 24, and pumps the gel 14 into the second conduit 30. The pump 18 can comprise any well-known type of pump which is suitable for use herewith, including a positive displacement pump, a gear pump, vane pump, screw pump, progressing cavity, lobe (or cam) pump, etc. Preferably, the pump 18 is very easy to clean and to maintain the sterility and cleanliness of the gel. For instance, a flexible tube (peristaltic) pump may be preferred.

The powered pump 18 may be located near the storage container 12. The powered pump 18 can include a switch 38 for turning the pump 18 on and off. The switch 38 may be located remotely from the pump 18 at a location such as on the floor. Otherwise it may be located on or near the transducer T. When the switch 38 is located on the floor, it is preferably activated by the technician's foot. When the switch 38 is located on or near the transducer T, it is preferably activated by the technician's hand.

When the pump is manually-operated, such as shown in FIG. 3, the pump 18 is preferably located outside of the cabinet B and near the technician so that the technician can easily access and use the pump 18. The manually-operated pump 18 has an internal compartment 40 which has a variable volume. The inlet 20 and outlet 22 each comprise a check valve (not shown) so that gel 14 can only flow into the compartment 40 through the inlet 20, and it can flow only out of the compartment 40 through the outlet 22. In use, the internal compartment 40 is expanded and contracted, thereby drawing gel 14 in from the storage container 12 via the first conduit 24, and out through the outlet 22. The manually-operated pump may be a foot-operated pump or it may be hand-operated. When it is hand-operated, it may have a mechanism, such as a trigger (not shown), which effectuates the change in internal volume of the compartment 40.

In a second embodiment hereof, and as shown schematically in FIG. 4, a storage container 112 for storing a quantity of gel 114 of at least one gallon is provided having an inlet 136 for receiving the gaseous fluid from a pump 118, and an outlet 116 for exiting the gel 114 from the storage container 112. The pump 118 can be connected directly to the container 112, otherwise it can be connected via a first conduit 124. Preferably, the pump 118 is a high-pressure, low-volume air pump. The pump 118 has an inlet 120 and an outlet 122 for delivering the gel 114 to a patient. The first conduit 124 has a first end 126 and a second end 128 to deliver the gaseous fluid from the pump 118 to the storage container 112. The first end 126 is connected to the outlet 122 of the pump 118 and the second end 128 is connected to the inlet 136 of the storage container 112, the inlet 136 preferably being located near the top of the storage container 112.

A disposable second conduit 130 including a disposable straw is provided having a first end 132 and a second end 134. The first end 132 is punctured into the outlet 116 of the storage container 112, similar to how intravenous tubing is spiked into an intravenous bag, and the second end 134 terminates at a location near the patient, wherein activating the pump 118 causes the gaseous fluid to flow through the first conduit 124, into the storage container 112, thereby becoming pressurized and exerting a force on the gel 114 in the storage container 112 which forces the gel 114 to the patient via the second conduit 130, which is secured to the transducer T. A disposable straw 135 is removably secured to the end 134, such as by friction or the like.

As understood by one having ordinary skill in the art, the gaseous fluid can comprise air or any other suitable type of gas which is non-reactive or corrosive with the gel 114, such as an inert gas. Preferably the gaseous fluid is air.

In order to maintain the sterility and cleanliness of the gel 14, an appropriate air filter can be used to filter all air passing through the pump 118 and into the container 112.

As show in FIG. 5, optionally there is provided a valve 40 for regulating the flow of gel 14 through the conduit 130. The valve 40 can comprise any suitable type of valve and can be operated either manually or remotely. It is to be appreciated that the valve can desirably be located near the second end 134 to keep any gel 14 from flowing out of the second conduit 130 after the pump 118 has turned off even after the straw 135 is removed.

Optionally, there can also be provided a pressure sensor 42 for measuring the pressure levels within the gel 14. Although the pressure sensor 42 can be positioned at any suitable location, such as in the storage container 112, it is preferably configured to measure a pressure gradient between the gel 14 in the storage container 112 and the gel 14 near the second end 134.

Furthermore, there can be provided means for controlling 44 which are electrically connected to the pressure sensor 42 and the pump 118. The means for controlling 44 can automatically turn the pump 118 on and off as needed to maintain a predetermined pressure gradient as measured by the pressure sensor 42. The means for controlling 44 can comprise any suitable controller or computing mechanism as determined by one having ordinary skill in the art. The means for controlling 44 can be either hardware-based or software-based.

It is also known that the rate of flow of the gel 14 through the conduit 130 is dependent, in part, upon the pressure gradient measured by the pressure sensor 42. Other factors, such as the viscosity of the gel 14 (which relates partially, in turn, to the temperature of the gel 14) and the head loss throughout the storage container 112 and the conduit 130 are known factors which impact the flow rate of the gel 14 out of the second end 134 of the conduit 130. The flow rate of the gel 14 can be increased by increasing the pressure gradient for the pump 118 to maintain.

Optionally, the apparatus 10 can include a temperature sensor 46 for measuring the temperature of the gel 14. The temperature sensor 46 can be electrically configured to provide a temperature reading to the means for controlling 44.

Optionally, the storage container 112 can be housed within a pressurizable housing 48 having an interior 49. In this regard, the pump 118 is configured to pressurize the storage container 112 within the housing 48, thereby applying the pressure to the gel 14 in the collapsible storage container 112 without having to plumb the pump 118 to the storage container 112 itself. Although the pump 118 is shown inside of the housing 48 in FIG. 5, it can alternatively be positioned outside the housing 48 as well. The storage container 112 can simply be placed into the housing 48 and the conduit 130 can pass out of the housing 48. Because maintaining the sterility and cleanliness of the gel 14 is a significant concern, the pressurizable housing 48 allows the gel 14 to be forced out of the storage container 112 without compromising any sanitary concerns. It also makes it easy for the technician to simply place the storage container 112 into the housing 48, connect the conduit 130 to the outlet 116 of the storage container 112, seal the housing 48, and allow the pump 118 to be turned on until the preset pressure gradient is achieved. The valve 40 is then opened and closed as needed for the gel 14 to be applied to the patient.

Optionally, the heat source 23 can comprise a warming plate 50 upon which the storage container 112 is placed. The heat source 23 can also be electrically configured to the means for controlling 44 so that the heat source 23 can be turned on or off to maintain the temperature of the gel 14 within a preset range as determined by the user.

Optionally, the means for controlling 44 can include inputs to manually adjust the temperature of the gel 14, the pressure gradient across the gel 14 (which equates directly to adjusting the flow rate of the gel 14), and so forth.

In this regard, it is seen the apparatus 10 can optionally be a stand-alone unit which does not require the computer CPU to act as the heat source 23. The apparatus 10 can then be positioned away from the computer CPU, such as under or on a desk, hung on a wall, placed on a shelf, located under a chair, or any other suitable location as desired by the technician.

Regardless of which embodiment is employed, in use the technician holds the transducer T and the attached second end 34 of the second conduit 30 over the patient's skin. The pump 18 is activated (or alternatively the valve 40 is opened), thereby delivering gel 14 to the patient via the second conduit 30. The technician maneuvers the second conduit 30 and the transducer T over the patient's skin so that the warmed gel 14 is placed on the patient's skin at the appropriate location(s). In this regard, the technician may either activate the pump 18 (or open the valve 40) by the switch 38 (if a powered pump is provided) located either on the floor using their foot, or by using their hand if the switch 38 is located on or near the transducer T, or by manually operating a manual pump (when provided). When the switch 38 is provided near the transducer T, the switch 38 is preferably positioned so that the technician can both operate the switch 38 and maneuver the transducer T and second conduit 30 easily with one hand.

It is noted that the technician may apply all of the gel 14 required for the procedure before beginning the procedure, or the technician may dispense the gel 14 as needed during the procedure. Currently, ultrasound technicians typically apply all of the gel required for the procedure before starting the procedure so that the gel 14 is hopefully only applied once as a matter of convenience. However, the present invention allows the technician to apply warmed gel 14 as needed.

It is to be appreciated by one having ordinary skill in the art that the present invention provides the technician with a simpler, easier-to-use mechanism for delivering gel to a patient. It is intended to decrease the overall time required for an ultrasound examination because the technician does not need to stop to apply additional gel before altogether relocating the desired image. Furthermore, the present invention provides the patient with warmed gel which is much more comfortable and helps the patient to relax during a potentially stressful procedure.

It should be understood that the present invention is not limited to the specific aspects described above. As stated above, the apparatus for delivering a warmed fluid may be used with any other suitable application in which a volume of a fluid is desired to be applied at a remote location.

As is apparent from the preceding, the present invention provides an apparatus for dispensing warmed gel for use with a medical device.

What is claimed is:

1. An apparatus for dispensing gel for use with an ultrasound machine comprising:
    an enclosed cabinet having a door and an access hole;
    an ultrasound machine disposed atop the cabinet, the ultrasound machine including a transducer;
    a storage container for storing a quantity of gel of at least one gallon, the storage container having an inlet to allow for air to enter the storage container and an outlet for exiting the gel from the storage container, the storage container being positioned within the enclosed cabinet and the second delivery conduit extending through the access hole of the enclosed cabinet;
    a pump for delivering the gel to a user, the pump having an inlet and an outlet;
    a first delivery conduit having a first end and a second end, the first end being punctured into the outlet of the storage container and the second end being connected to the inlet of the pump, the first delivery conduit being disposable after each use;
    a second delivery conduit having a first end and a second end, the first end being connected to the outlet of the pump, the second delivery conduit being juxtaposed and secured to about the transducer, the second delivery conduit including a straw, the straw being disposable after each use;
    a heat source for heating the gel in the storage container to a temperature of about 80° F. to about 100° F., the heat source being a computer CPU, the CPU being positioned within the enclosed cabinet; and
    wherein the gel is administered to the user, as needed, as the transducer traverses the user's body.

2. The apparatus of claim 1 wherein the pump is a manually operated pump.

3. The apparatus of claim 1 wherein the pump is a powered pump.

4. The apparatus of claim 1 wherein the storage container is formed of a polymer.

5. An apparatus for use with an ultrasound machine for dispensing gel comprising:
    an ultrasound machine including a transducer;
    a collapsible storage container for storing a quantity of gel of at least one gallon, the storage container having an outlet;
    a housing having an internal chamber for housing the storage container;
    a pump for pressurizing the internal chamber and the storage container with a gaseous fluid to the storage container, the pump having an inlet and an outlet, the pump outlet being in fluid communication with the internal chamber;
    a heat source comprising a heating plate upon which the storage container is placed for heating the gel to a temperature of about 80° F. to about 100° F.; and
    a flexible delivery conduit having a first end and a second end, the first end being punctured into the outlet of the storage container and the second end extending outwardly of the housing to a distal location, the delivery conduit including a straw, the straw being disposable after each use.

6. The apparatus of claim 5 including a valve for regulating flow of the gel through the delivery conduit.

7. The apparatus of claim 5 including a temperature sensor positioned within the housing for monitoring the temperature of the gel.

8. The apparatus of claim 5 wherein the storage container is formed of a polymer.

* * * * *